United States Patent
Winter et al.

(10) Patent No.: US 6,320,068 B1
(45) Date of Patent: Nov. 20, 2001

(54) PREPARATION OF ARYLPHOSPHINES

(75) Inventors: Stephen Benedict David Winter; Ian Campbell Lennon, both of Cambridge (GB)

(73) Assignee: Chirotech Technology, Ltd. (GB)

( * ) Notice: Subject to any disclaimer, the term of this patent is extended or adjusted under 35 U.S.C. 154(b) by 0 days.

(21) Appl. No.: 09/700,456

(22) PCT Filed: Jun. 30, 1999

(86) PCT No.: PCT/GB99/02065

§ 371 Date: Nov. 15, 2000

§ 102(e) Date: Nov. 15, 2000

(87) PCT Pub. No.: WO00/00498

PCT Pub. Date: Jan. 6, 2000

(30) Foreign Application Priority Data

Jun. 30, 1998 (GB) .................................................. 9814170

(51) Int. Cl.$^7$ .................................................. C07C 69/76
(52) U.S. Cl. ................. 560/8; 560/100; 564/134
(58) Field of Search ........................ 560/8, 100; 564/134

(56) References Cited

U.S. PATENT DOCUMENTS 5,399,771 * 3/1995 Cai et al. .

FOREIGN PATENT DOCUMENTS 9312260   6/1993 (WO) .
9924444   5/1999 (WO) .

OTHER PUBLICATIONS

Gilbertson et al, Journal of Organic Chemistry, 61(9), pp. 2922–2923 and Suplemental material provided by Applicants.*

Ager et al, Chemical Communications, 24 (21) pp. 2359–2360.*

Herd et al, Journal of Organometallic Chemistry, 522, (1)69–76.*

Gilbertson, S. R. et al. (1996) "Palladium–Catalyzed Synthesis of Phosphine–Containing Amino Acids" *Journal of Organic Chemistry* 61(9):2922–2923.

Herd, O. et al. (1996) "Water Soluble Phosphines VIII. Palladium–Catalyzed P-C Cross Coupling Reactions Between Primary or Secondary Phosphines and Functional Aryliodides—A Novel Synthetic Route to Water Soluble Phosphines" *Journal of Organometallic Chemistry* 522(1):69–76.

Wilson, S. R. et al. (1990) "Preparation of a New Class of C2–Symmetric Chiral Phosphines: The First Asymmetric Staudinger Reaction" *Synlett* (4):199–200.

Ager, D. J. et al. (1997) "Convenient and Direct Preparation of Tertiary Phosphines Via Nickel–Catalysed Cross–Coupling" *Chemical Communications* 24(21):2359–2360.

Gilbertson, S. R. et al. (1996) Supplementary Material for "Palladium–Catalyzed Synthesis of Phosphine–Containing Amino Acids" *Journal of Organic Chemistry* 61(9):2922–2923, supplemental pp. 1–10.

* cited by examiner

*Primary Examiner*—Gary Geist
*Assistant Examiner*—Hector M Reyes
(74) *Attorney, Agent, or Firm*—Saliwanchik, Lloyd & Saliwanchik

(57) ABSTRACT

The present invention pertains to a process for the preparation of an arylphosphine of the formula $R^1OC\text{---}Ar\text{---}PR^2R^3$ wherein Ar is aryl or heteroaryl; $R^1$ is an alkoxy or amine group; and $R^2$ and $R^3$ are each any organic group; and each of the respective groups may optionally be substituted with any non-interfering group; which comprises the reaction of a sulfonyloxy compound of the formula $R^1OC\text{---}Ar\text{---}OSO_2R^4$ wherein $R^4$ is alkyl, haloalkyl, perhaloalkyl, aryl, aralkyl or alkaryl, with a phosphine of the formula $HPR^2R^3$, in a solvent and in the presence of a palladium catalyst and a base. The arylphosphine can then readily be converted to a chiral phosphine ligand.

29 Claims, No Drawings

PREPARATION OF ARYLPHOSPHINES

CROSS-REFERENCE TO RELATED APPLICATIONS

This application is a U.S. national stage application of International patent Application No. PCT/GB99/02065, filed Jun. 30, 1999, which claims priority from U.S. Provisional Application No. 60/096,174, filed Aug. 11, 1998.

FIELD OF THE INVENTION

This invention relates to processes suitable for the large scale preparation of arylphosphines. especially those useful as ligand precursors or ligands in asymmetric allylic substitution catalysts.

BACKGROUND OF THE INVENTION

Chiral phosphine ligands such as (1) and (2)

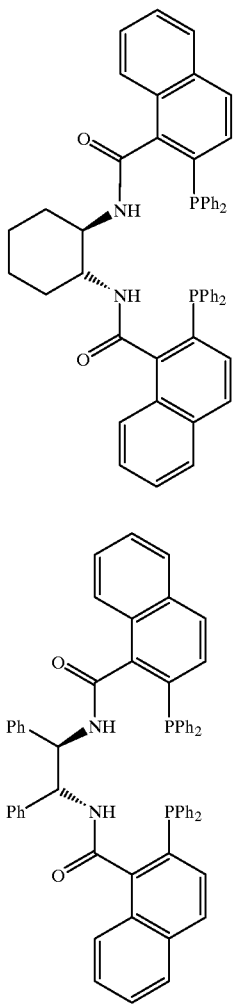

and the opposite enantiomers thereof, have been shown to be effective in palladium(0)-catalysed asymmetric allylic substitution reactions. For a review, see Trost and Van Vranken, Chem Rev. (1996) 96: 395. See also U.S. Pat. No. 5,739,396.

Such catalysts are eminently suitable for industrial applications, especially for the provision of chiral pharmaceutical intermediates such as phthalimidovinyl glycinol, in high enantiomeric purity. For this purpose, and in other industrial applications such as flavour and fragrance fine chemicals, the development of manufacturing processes requires in turn large amounts of a ligand such as (1) or (2), e.g. in kilogram quantity or greater. Thus, there is a requirement for efficient and scaleable methods for synthesis of such ligands.

A key intermediate in the synthesis of these ligands is 2-diphenylphosphino-1-naphthoic acid and derivatives thereof. Several processes for the synthesis of arylphosphines from aryl triflates have been described in the literature.

For example, WO-A-9312260 and U.S. Pat. No. 5,739,396 disclose the reaction of trimethylsilyldiphenylphosphine, an aryl iodide and bis(benzonitrile)palladium dichloride in toluene at reflux. Trimethylsilyldiphenylphosphine is expensive and not readily available. This procedure gives only moderate yields (60%) and requires silica chromatography for purification of the product. Bis(benzonitrile)palladium dichloride is also expensive, and a high catalyst loading is used (5 mol %).

Another known process comprises the reaction of an aryl triflate with chlorodiphenylphosphine, a reductant (zinc) and a nickel catalyst in DMF at 100° C.; see Ager et al, Chem. Commun. (1997) 2359. This procedure typically requires a high catalyst loading (4–10 mol %) and can involve prolonged heating at reflux. The nickel catalyst is highly toxic and, as well as considerations for operator safety and residue disposal, filtration through a plug of silica is typically required to remove the catalyst.

Cai et al, J. Org. Chem. (1994) 59:7180–1, and U.S. Pat. No. 5,399,771 disclose the preparation of BINAP using the appropriate aryl triflate with diphenylphosphine. The preferred catalyst is nickel, palladium catalysis giving no reaction al all. Cai et al reports that DMF is the only satisfactory solvent. A chelating phosphine was also present.

Gilbertson et al, J. Org. Chem. (1996) 61:2922–3, discloses the palladium-catalysed conversion of aryl triflates, specifically tyrosine derivatives, to the corresponding aryl diphenylphosphines, by reaction with diphenylphosphine. The solvent is DMSO. It is reported that the reaction does not take place in DMF, using palladium. The Supplementary Material shows that 5 mol % of each of the catalyst Pd(OAC)$_2$ and 1,4-bis(diphenylphosphino)butane, i.e. a chelating phosphine, are used. Isolation of pure aryl diphenylphosphine products requires conversion to the corresponding phosphine sulfide, column chromatography and desulfurization with Raney nickel.

Reaction of diphenylphosphine, a base, palladium catalyst and aryl iodide (or bromide) also gives the corresponding triarylphosphine; see Werd et al, J. Organomet. Chem. (1996), 522: 69. For the synthesis of ligand (1) or (2), however, a 2-iodo- or 2-bromo-1-naphthoic acid derivative is not readily accessible.

SUMMARY OF THE INVENTION

The present invention is based on the discovery of an alternative process for preparing aryl phosphines, which allows the limitations of the prior art to be overcome. In particular, it has been discovered that an aryl sulfonyloxy compound can participate in a cross-coupling reaction with diphenylphosphine and palladium catalyst, without many of the restrictions that prejudice the development of an efficient, scaleable and economical synthesis of phosphines. The invention concerns the use of sulfonyloxy derivatives, readily prepared from the parent phenol, with a phosphine (HPR$^2$R$^3$), a base and palladium catalyst, in the following reaction:

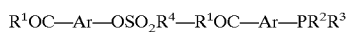

R$^1$OC—Ar—OSO$_2$R$^4$→R$^1$OC—Ar—PR$^2$R$^3$

The group R$^1$ may be an alkoxy or amino group. The groups R$^2$ and R$^3$ are any hydrocarbon group including, for example, aryl and alkyl. The group R$^4$ may be an aryl or alkyl group including those with halogen substitution.

Each of the respective R groups may optionally be substituted with one or more non-interfering group. Each such group may be of, for example, up to 20 C atoms.

One advantage of this invention is that no chelating phosphine is required. Another is that the solvent is not critical, thereby allowing the use of common, easy-to-handle organic solvents such as toluene and acetonitrile. Without wishing to be bound by theory, these two factors may be linked.

A further advantage of the invention is that the catalyst loading need not be especially high. For example, it is typically less than 1%, and often less than 0.5% (mol % relative to sulfonate). In particular, one-to-one stoichiometries of the phosphine and sulfonyloxy compound may be used, and with low catalyst loadings, for example 0.4 mol %, purification of the product is relatively simple.

In summary, this invention allows the aryl phosphine to be manufactured economically on a large scale. Material of reproducible quality can be manufactured in high yields.

DESCRIPTION OF THE INVENTION

Ar may represent any aromatic nucleus, mono or polycyclic, with or without hetero atoms such as N, O or S. Although the respective points of substitution of the COR$^1$ and PR$^2$R$^3$ groups on the nucleus are not thought to be critical, they are typically in 1,2, 1,3 or 1,4-relationship on a benzene ring that is optionally otherwise substituted and/or fused to another ring or ring system. Thus, for example, a starting material for use in the invention may have the formula

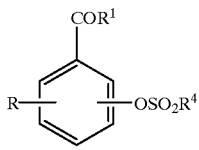

wherein R is any non-interfering substituent and/or represents a fused ring.

Ar is most preferably naphthyl. R$^1$ is preferably alkoxy, more preferably methoxy.

A preferred embodiment of the present invention is a process for the preparation of 2-diphenylphosphino-1-naphthoic acid and derivatives thereof, for example those compounds therein where R$^2$ and R$^3$ are both phenyl and R$^1$OC—Ar is 1-carboalkoxy-2-naphthyl. See the reaction shown in Example 1.

The preferred catalyst for this invention is a palladium (II) salt, more preferably palladium (II) acetate. The preferred base is a tertiary amine, more preferably triethylamine. The preferred groups for R$^4$ are perfluoroalkyl groups, including trifluoromethyl and perfluoro-1-butyl.

Typically the reagents are heated together at reflux in an appropriate solvent, for example toluene or acetonitrile, e.g. for approximately 16 hours. The solvent can be much less volatile than DMSO, e.g. boiling below 125° C. Progress of the reaction may be monitored by TLC or taking aliquots for analysis by $^1$H NMR or $^{31}$P NMR.

The following Examples illustrate the present invention. The Preparations illustrate starting materials.

Preparation 1 Methyl 2-hydroxy-1-naphthoate

Dicyclohexyicarbodiimide (1.20 Kg, 5.8 mol, 1.1 eq) was added portionwise over 4.5 hours to a cooled, mechanically-stirred slurry of 2-hydroxy-1-naphthoic acid (1.00 Kg, 5.3 mol) in methanol (3 L) under nitrogen. The internal temperature was maintained between 10 and 15° C. during the addition. Once the addition was complete, the mixture was allowed to warm to ambient temperature and stirred for 16 hours. The methanol was removed under reduced pressure and the residue taken up in ethyl acetate (5 L) and heated with stirring to 64° C. (internal temperature) and then allowed to cool once again to ambient temperature. The mixture was filtered, and the solid washed with ethyl acetate (0.7 L). The ethyl acetate solutions were combined and concentrated under reduced pressure. The residue (2.5 Kg) was recrystallised from ethanol-water (9:1, 3.3 L) and dried under vacuum at ambient temperature. Yield 0.92 Kg, 85%

Preparation 2 Methyl 2-trifluoromethanesulfonyloxy-1-naphthoate

Trifluoromethanesulfonic anhydride (492 g, 1.74 mol, 1.1 eq) in dichloromethane (0.5 L) was added over 1.5 hours to a suspension of methyl 2-hydroxy-1-naphthoate (319 g, 1.58 mol) and pyridine (330 ml, 4.08 mol, 2.6 eq) in dichloromethane (1.7 L) maintained at an internal temperature between −70 and −50° C., under nitrogen. Once the addition was complete, the mixture was allowed to warm to ambient temperature and stirred for 16 hours, after which time all solids had dissolved. Methyl tert-butyl ether (MTBE, 2.5 L) was added, causing precipitation. The solids were removed by filtration and washed with MTBE (0.5 L). The MTBE solutions were combined and washed with 2 N HCl(aq) (0.3 L then 0.2 L), water (2×2.5 L) and brine (2 L). The organic layer was dried (MgSO$_4$), filtered and concentrated under reduced pressure. The residue was dissolved in toluene (2.5 L) and washed with 1 N NaOH (aq) (0.5 L), water (2.5 L) and brine (1 L). The toluene solution was dried (MgSO$_4$), filtered and concentrated under reduced pressure. Initially a slightly brown oil, the product crystallised on standing. Yield 438.5 g, 83%

Preparation 3 Methyl 2-trifluoromethanesulfonyloxysalicylate

Trifluoromethanesulfonic anhydride (28.4 mL, 169 mmol, 1.1 eq) was added to a solution of methyl salicylate (20 mL, 154 mmol) and pyridine (31 mL, 385 mmol, 2.5 eq) in dichloromethane (150 mL) maintained at an internal temperature about −40° C., under nitrogen. Once the addition was complete, the mixture was allowed to warm to ambient temperature and stirred for 16 hours. Toluene (150 mL) was added causing precipitation. The solids were removed by filtration and washed with toluene (20 mL). The organic solutions were combined and washed with 2 N HCl (aq) (2×50 mL), water (100 mL), saturated aqueous sodium carbonate solution (100 mL) and brine (100 mL). The organic layer was dried (MgSO$_4$), filtered and concentrated under reduced pressure. Yield 41.93 g, 96%

Preparation 4 Methyl 2-(perfluoro-1-butanesulfonyloxy)-1-napthoate

Perfluoro-1-butanesulfonyl fluoride (19 mL, 106 mmol, 1 eq) was added to a solution of methyl 2-hydroxy-1-naphthoate (21.25 g, 105 mmol, 1 eq) and triethylamine (15 mL, 108 mmol, 1 eq) in tetrahydrofuran (150 mL) maintained at an internal temperature about 0° C., under nitrogen. Once the addition was complete, the mixture was allowed to warm to ambient temperature and stirred for 64 hours. Toluene (150 mL) was added causing some precipitation. The solids were removed by filtration through Celiteä and washed with toluene (20 mL). The organic solutions were combined and washed with 2 N HCl (aq) (2×50 mL), water (100 mL), saturated aqueous sodium carbonate solution (100 mL) and brine (100 mL). The organic layer was dried (MgSO$_4$), filtered and concentrated under reduced pressure. Yield 48.79 g, 95%

EXAMPLE 1

Methyl 2-diphenylphosphino-1-naphthoate

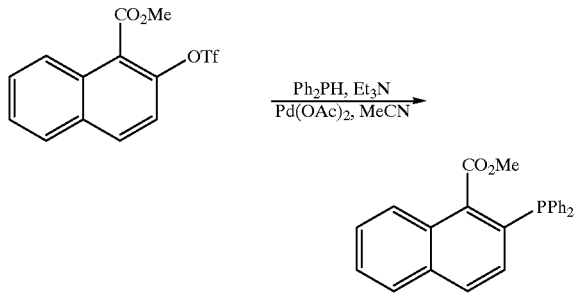

A stirred solution of methyl 2-trifluoromethanesulfonyloxy-1-naphthoate (52.7 g, 158 mmol, 1 eq), triethylamine (26.5 ml, 190 mmol, 1.2 eq) and palladium acetate (0.15 g, 0.7 mmol, 0.004 eq) in acetonitrile (600 ml) was sparged with nitrogen for 30 minutes. Diphenylphosphine (29.4 g, 158 mmol, 1 eq) was added instantly giving a red coloration. The solution was heated at reflux under nitrogen for 17 hours. The blood-red solution was allowed to cool and concentrated under reduced pressure to approximately half its original volume. Methanol (50 ml) was added and the mixture concentrated a little more under reduced pressure. The product crystallised from this mixture and was collected by filtration and washed with ice-cold methanol (200 ml) and dried under vacuum at ambient temperature; $^{31}$p NMR (162 mHz; CDCl$_3$): δ−7.8. Yield 54.1 g, 92%

The product may be converted to a ligand (1) or (2) or the opposite enantiomer thereof, by known procedures.

EXAMPLE 2

Methyl 2-diphenylphosphino-1-naphthoate from methyl 2-(perfluoro-1-butanesulfonyloxy)-1-naphthoate Diphenylphosphine (0.51 mL g, 2.93 mmol, 1 eq) was added to a stirred solution of methyl 2-perfluoro-1-butanesulfonyloxy-1-naphthoate (1.431 g, 2.95 mmol, 1 eq), triethylamine (0.45 mL, 3.23 mmol, 1.1 eq) and palladium acetate (0.005 g, 0.02 mmol, 0.007 eq) in degassed acetonitrile (10 mL) instantly giving a red coloration. The solution was heated at reflux under nitrogen for 17 hours. The blood-red solution was allowed to cool and an aliquot taken for NMR analysis.

$^{31}$P NMR showed complete consumption of diphenylphosphine and formation of substantially one product, the desired triarylphosphine, identical to that described in Example 1.

EXAMPLE 3

Methyl 2-diphenylphosphino-1-naphthoate (toluene as solvent)

Diphenylphosphine (0.72 mL, 4.14 mmol, 1 eq) was added to a stirred solution of methyl 2-trifluoromethanesulfonyloxy-1-naphthoate (1.389 g, 4.16 mmol, 1 eq), triethylamine (0.64 mL, 4.59 mmol, 1.1 eq) and palladium acetate (0.005 g, 0.02 mmol, 0.005 eq) in degassed toluene (10 mL) instantly giving a red coloration. The solution was heated at reflux under nitrogen for 17 hours. The blood-red solution was allowed to cool and an aliquot taken for NMR analysis.

31P NMR showed complete consumption of diphenylphosphine and formation of substantially one product, the desired triarylphosphine, identical to that described in Example 1.

EXAMPLE 4

Methyl 2-diphenylphosphino-1-naphthoate (DMF as solvent)

Diphenylphosphine (0.72 mL, 4.14 mmol, 1 eq) was added to a stirred solution of methyl 2-trifluoromethanesulfonyloxy-1-naphthoate (1.384 g, 4.14 mmol, 1 eq), triethylamine (0.64 mL, 4.59 mmol, 1.1 eq) and palladium acetate (0.005 g, 0.02 mmol, 0.005 eq) in degassed DMF (10 mL) instantly giving a red coloration. The solution was heated at reflux under nitrogen for 17 hours. The blood-red solution was allowed to cool and an aliquot taken for NMR analysis.

$^{31}$P NMR showed complete consumption of diphenylphosphine and formation of substantially one product the desired triarylphosphine, identical to that described in Example 1.

EXAMPLE 5

Methyl 2-Diphenylphosphino-1-naphthoate (DMSO as solvent)

Diphenylphosphine (0.72 mL, 4.14 mmol, 1 eq) was added to a stirred solution of methyl 2-trifluoromethanesulfonyloxy-1-naphthoate (1.373 g, 4.11 mmol, 1 eq), triethylamine (0.64 mL, 4.59 mmol, 1.1 eq) and palladium acetate (0.005 g, 0.02 mmol, 0.005 eq) in degassed DMSO (10 mL) instantly giving a red coloration. The solution was heated at reflux under nitrogen for 17 hours. The blood-red solution was allowed to cool and an aliquot taken for NMR analysis.

$^{31}$P NMR showed complete consumption of diphenylphosphine and formation of the desired triarylphosphine as the major product, and a second product (ca 25% of mixture), having a chemical shift consistent with the oxide of triarylphosphine, δ (162 MHz, CDCl$_3$) +31.2.

EXAMPLE 6

Methyl 2-diphenylphosphino-1-naphthoate (acetonitrile as solvent, with 1,4-bis(diphenylphosphino)butane additive)

Diphenylphosphine (0.55 mL, 3.16 mmol, 1 eq) was added to a stirred solution of methyl 2-trifluoromethanesulfonyloxy-1-naphthoate (1.047 g, 3.13 mmol, 1 eq), triethylamine (0. 5 mL, 3.59 mmol, 1.1 eq), 1,4-bis(diphenylphosphino)butane (dppb) (0.03 g, 0.07 mmol, 0.02 eq) and palladium acetate (0.005 g, 0.02 mmol, 0.006 eq) in degassed MeCN (10 mL) instantly giving a red coloration. The solution was heated at reflux under nitrogen for 17 hours. The blood-red solution was allowed to cool and an aliquot taken for NMR analysis.

$^{31}$P NMR showed complete consumption of diphenylphosphine and formation of the desired triarylphosphine as the major product, and a second product (ca 32% of mixture), having a chemical shift consistent with the oxide of triarylphosphine, δ (162 MHz, CDCl$_3$)+31.2.

EXAMPLE 7

Methyl 2-diphenylphosphinobenzoate

Diphenylphosphine (0.94 mL, 5.40 mmol, 1 eq) was added to a stirred solution of methyl 2-trifluoromethanesulfonyloxybenzoate (1.531 g, 5.39 mmol, 1 eq), triethylamine (0.85 mL, 6.1 mmol, 1.1 eq) and palladium acetate (0.005 g, 0.02 mmol, 0.004 eq) in degassed MeCN (10 mL) instantly giving a red coloration. The solution was heated at reflux under nitrogen for 17 hours. The blood-red solution was allowed to cool and an aliquot taken for NMR analysis.

$^3$P NMR showed complete consumption of diphenylphosphine and formation of substantially one product the desired triarylphosphine, δ (162 MHz CDC$_3$)–3.3.

What is claimed is:

1. A process for preparation of an arylphosphine of the formula

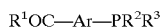

$R^1OC-Ar-PR^2R^3$ wherein Ar is aryl or heteroaryl; $R^1$ is an alkoxy or amine group, and $R^2$ and $R^3$ are each any organic group; and each of the respective groups may optionally be substituted with any non-interfering group; which comprises the reaction of a sulfonyloxy compound of the formula

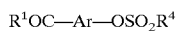

$R^1OC-Ar-OSO_2R^4$ wherein $R^4$ is alkyl, haloalkyl, perhaloalkyl, aryl, aralkyl or alkaryl, with a secondary or primary phosphine of the formula $HPR^2R^3$, in a solvent and in the presence of a palladium catalyst and a base.

2. The process according to claim 1, wherein the catalyst is a palladium (II) salt.

3. The process according to claim 2, wherein the catalyst is palladium (II) acetate.

4. The process according to claim 1, wherein the base is a tertiary amine.

5. The process according to claim 4, wherein the base is triethylamine.

6. The process according to claim 1, wherein $R^2$ and $R^3$ are each aryl or alkyl.

7. The process according to claim 6, wherein $R^2$ and $R^3$ are each optionally substituted phenyl.

8. The process according to claim 1, wherein Ar bears the COR$^1$ and OSO$_2$R$^4$ groups in a 1,2-relationship.

9. The process according to claim 1, wherein the sulfonyloxy compound has the formula

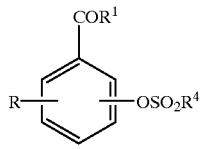

wherein R is any non-interfering substituent and/or represents a fused ring.

10. The process according to claim 8, wherein Ar is naphthyl.

11. The process according to claim 1, wherein $R^1$ is alkoxy.

12. The process according to claim 8, wherein the arylphosphine has the formula

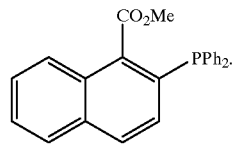

13. The process according to claim 1, wherein $R^4$ is perfluoroalkyl.

14. The process according to claim 13, wherein $R^4$ is trifluoromethyl.

15. The process according to claim 13, wherein $R^4$ is perfluoro-1-butyl.

16. The process according to claim 1, wherein the solvent has a boiling point below 125° C.

17. The process according to claim 16, which additionally comprises concentrating the arylphosphine by removal of the solvent under reduced pressure.

18. The process according to claim 16, wherein the solvent is an aromatic hydrocarbon.

19. The process according to claim 18, wherein the solvent is toluene.

20. The process according to claim 16, wherein the solvent is acetonitrile.

21. The process according to claim 1, wherein the reaction mixture is substantially free of chelating phosphine.

22. The process according to claim 1, wherein the catalyst loading is less than 1%.

23. The process according to claim 22, wherein the catalyst loading is less than 0.5%.

24. The process according to claim 1, which comprises the additional step of converting the arylphosphine to a chiral phosphine ligand.

25. The process according to claim 24, wherein the chiral phosphine ligand is an enantiomerically enriched compound of formula (1) or (2)

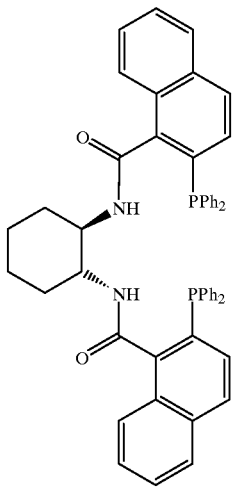

(1)

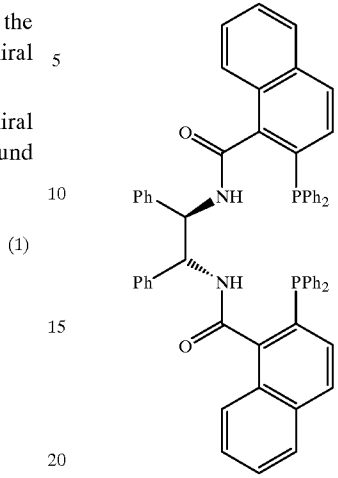

(2)

or the opposite enantiomer thereof.

26. The process according to claim 11, wherein $R^1$ is methoxy.

27. The process according to claim 17, wherein the solvent is an aromatic hydrocarbon.

28. The process according to claim 27, wherein the solvent is toluene.

29. The process according to claim 17, wherein the solvent is acetonitrile.

* * * * *